US011839601B2

(12) United States Patent
Eyal

(10) Patent No.: US 11,839,601 B2
(45) Date of Patent: *Dec. 12, 2023

(54) CANNABIS-ENRICHED ENZYMATICALLY TREATED THERAPEUTIC COMPOSITION

(71) Applicant: Canabuzz-Med, Or-Akiva (IL)

(72) Inventor: Aharon M. Eyal, Jerusalem (IL)

(73) Assignee: CANNA-B CURE LTD, Or-Akiva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/094,642

(22) PCT Filed: Apr. 18, 2017

(86) PCT No.: PCT/IB2017/052214
§ 371 (c)(1),
(2) Date: Oct. 18, 2018

(87) PCT Pub. No.: WO2017/182950
PCT Pub. Date: Oct. 26, 2017

(65) Prior Publication Data
US 2019/0105298 A1 Apr. 11, 2019

Related U.S. Application Data

(60) Provisional application No. 62/324,594, filed on Apr. 19, 2016, provisional application No. 62/324,577, filed on Apr. 19, 2016.

(51) Int. Cl.
| | |
|---|---|
| *A61K 31/352* | (2006.01) |
| *A61P 25/28* | (2006.01) |
| *A61P 25/22* | (2006.01) |
| *A61P 1/00* | (2006.01) |
| *A61P 25/08* | (2006.01) |
| *A61P 25/16* | (2006.01) |
| *A61K 31/05* | (2006.01) |
| *A61K 31/191* | (2006.01) |
| *A61K 31/7004* | (2006.01) |
| *A61K 35/644* | (2015.01) |
| *A23L 33/105* | (2016.01) |
| *A23L 33/125* | (2016.01) |
| *A23L 33/10* | (2016.01) |

(52) U.S. Cl.
CPC ............ *A61K 31/352* (2013.01); *A23L 33/10* (2016.08); *A23L 33/105* (2016.08); *A23L 33/125* (2016.08); *A61K 31/05* (2013.01); *A61K 31/191* (2013.01); *A61K 31/7004* (2013.01); *A61P 1/00* (2018.01); *A61P 25/08* (2018.01); *A61P 25/16* (2018.01); *A61P 25/22* (2018.01); *A61P 25/28* (2018.01); *A61K 35/644* (2013.01)

(58) Field of Classification Search
CPC .. A61K 31/352; A61K 31/05; A61K 31/7004; A61K 31/191; A61K 35/644; A61P 25/08; A61P 25/16; A61P 25/28; A61P 1/00; A61P 25/22
USPC ......................................................... 514/23
See application file for complete search history.

(56) References Cited

U.S. PATENT DOCUMENTS

| 5,385,827 | A | * | 1/1995 | Clark | ................. C22B 3/18 |
| | | | | | 435/14 |
| 5,605,697 | A | * | 2/1997 | Asano | ................. A21D 2/14 |
| | | | | | 424/439 |
| 8,445,034 | B1 | | 5/2013 | Coles, Jr. | |
| 2001/0006687 | A1 | | 7/2001 | Postmes | |
| 2009/0202613 | A1 | * | 8/2009 | Tabatchnick | ............ A23L 33/19 |
| | | | | | 424/439 |
| 2014/0302086 | A1 | | 10/2014 | Kelly | |
| 2015/0297644 | A1 | | 10/2015 | Park et al. | |

FOREIGN PATENT DOCUMENTS

| CN | 1101510 A | 4/1995 |
| WO | 2015/068052 | 5/2015 |
| WO | WO 2017013661 A1 * | 1/2017 |
| WO | 2017/072704 A1 | 5/2017 |

OTHER PUBLICATIONS

Newseed; https://www.foodsweeteners.com; Jul. 8, 2015.*
Wagner et al. (Food Technology & Processing, Nov. 2008).*
U.S. Appl. No. 62/324,594 to , filed Apr. 19, 2016.
U.S. Appl. No. 62/324,577 to , filed Apr. 19, 2016.
Official Communication issued in International Bureau of WIPO Patent Application No. PCT/IB2017/052214, dated Jul. 17, 2017.
Kwakman, Paulus HS and Zaat, Sebastian AJ. "Antibacterial components of honey", IUBMB Life, Epub Nov. 17, 2011, p. 48-55, vol. 64, issue 1, John Wiley & Sons, Inc, Hoboken, NJ, USA.

* cited by examiner

*Primary Examiner* — Layla D Berry
(74) *Attorney, Agent, or Firm* — ALPHAPATENT ASSOCIATES, LTD; Daniel J. Swirsky

(57) ABSTRACT

A cannabis-enriched enzymatically treated therapeutic composition. A therapeutic composition is described including water, glucose, glucose reaction product other than sucrose and fructose; a selected amount of a cannabinoid, a cannabinoid reaction product; optionally a terpene and optionally a terpene reaction product. Methods of making and using the compositions are also described.

16 Claims, No Drawings

CANNABIS-ENRICHED ENZYMATICALLY TREATED THERAPEUTIC COMPOSITION

CROSS-REFERENCE TO RELATED APPLICATIONS

This application claims the benefit under 35 U.S.C. § 119(e) of U.S. Provisional Application Ser. Nos. 62/324,577 and 62/324,594, both filed on Apr. 19, 2016, the disclosures of which are expressly incorporated by reference herein in their entirety.

TECHNICAL FIELD

The field of art to which this invention generally pertains is cannabinoid compositions, and specifically cannabinoid compositions for therapeutic use.

BACKGROUND OF THE INVENTION

There is a great need for cannabis therapeutic compositions to provide controlled and personalized therapeutic effect. Furthermore, there is a need for an enhanced therapeutic effect so that a composition of relatively low cannabinoids concentration has a strong therapeutic effect.

SUMMARY OF THE INVENTION

A therapeutic composition is described including (i) water at a concentration in the range of up to 30% by weight, (ii) glucose, (iii) at least 5 parts per million glucose reaction product other than sucrose and fructose; (iii) a selected amount of a cannabinoid, (iv) at least 1 parts per million cannabinoid reaction product; optionally (v) a terpene and optionally (vi) at least 1 parts per million terpene reaction product.

Additional embodiments include: the therapeutic composition described above where said glucose reaction product comprises glucono-lactone, gluconic acid and combinations thereof; the therapeutic composition described above where said glucose reaction product is a product of glucose oxidation, wherein said cannabinoid reaction product is a product of cannabinoid oxidation and/or wherein said terpene reaction product is a product of terpene oxidation; the therapeutic composition described above where the glucose to glucose reaction product weight/weight ratio is in the range of between 1 and 1000, wherein the cannabinoid to cannabinoid reaction product weight/weight ratio is in the range of between 1 and 1000, and/or wherein the terpene to terpene reaction product weight/weight ratio is in the range of between 1 and 1000; the therapeutic composition described above where said composition is homogeneous; the therapeutic composition described above comprising said cannabinoid in a concentration of at least 0.1 parts per million and less than 2% by weight; the therapeutic composition described above having an enhanced therapeutic effect compared with that of a composition comprising the same cannabinoid amounts, but not containing said glucose reaction product and not containing said cannabinoid reaction product; the therapeutic composition described above where said therapeutic effect, is for treating a condition selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease; the therapeutic composition described above containing a selected amount of a cannabinoid reaction product, where the cannabinoid reaction product is a cannabinoid oxidation product, and having an enhanced therapeutic effect, compared with that of a composition comprising the same cannabinoid amounts and no cannabinoid oxidation product; the therapeutic composition described above where said therapeutic effect, is for treating an condition selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease; the therapeutic composition described above containing a selected amount of a terpene reaction product and having an enhanced therapeutic effect, compared with that of a composition comprising the same cannabinoid amounts and no terpene reaction product; and the therapeutic composition described above where said therapeutic effect, is for treating an condition selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

A method of treating a medical condition is also described including administering to a subject an effective amount of the therapeutic composition described above; the therapeutic composition described above additionally containing a non-cannabis pharmaceutical compound; the method of treating a medical condition comprising administering to a subject an effective amount of the therapeutic composition described above.

A method for producing a therapeutic composition is also described including providing a glucose-containing composition; providing a cannabinoid-containing composition; blending said glucose-containing composition with said cannabinoid-containing composition to form cannabinoid-enriched glucose composition; applying an enzyme at a selected temperature, a selected pH, and a selected water activity and for a selected duration, to said cannabinoid-enriched glucose composition, whereby an enzymatically-catalyzed conversion of at least one of glucose and cannabinoid is produced and optionally removing water from said cannabinoid-enriched glucose composition and where said temperature, pH, water activity and duration are selected to enzymatically-catalyze the conversion of at least 0.1% by weight of said glucose, said cannabinoid or both.

Additional embodiments include: the method described above where said temperature, pH, and water activity are selected to reach the desired degree of conversion within a duration of less than a week; the method described above where said applied enzyme is a honey enzyme; the method described above where said honey enzyme is selected from the group consisting of glucose oxidase, invertase, diastase, catalase, acid phosphatase and combinations thereof; the method described above where said applied enzyme comprises a non-honey enzyme; the method described above where the glucose concentration in said cannabinoid-enriched glucose composition is greater than 30% by weight; the method described above where said cannabinoid-enriched glucose composition, additionally contains water, and wherein the water concentration there is less than 60% by weight; the method described above where glucose to water weight/weight ratio in said cannabinoid-enriched glucose composition is greater than 2; the method described above where said glucose-containing composition additionally contains sucrose; the method described above where said glucose-containing composition comprises honey; the method described above where said cannabinoid-containing composition comprises a cannabis plant extract; the method described above where said blending includes adding an emulsifier; the method described above where said cannabinoid-enriched glucose composition is homogeneous; the method described above where the glucose to cannabinoid weight/weight ratio in said cannabinoid-enriched glucose composition is greater than 10; the method described above where said selected temperature is in the range of between 20° C. and 70° C.; the method described above where said applying an enzyme comprises inducing enzyme activity and wherein said inducing comprises water addition; the method described above where said applying an enzyme comprises introduction into the honey stomach of a honeybee; the method described above including additionally blending said cannabinoid-enriched glucose composition with a non-cannabis pharmaceutical compound; the method described above where said cannabinoid-containing composition comprises tetrahydrocannabinol, and where said therapeutic composition comprises at least 0.1 parts per million tetrahydrocannabinol, and less than 1% by weight tetrahydrocannabinol; the method described above where said cannabinoid-containing composition comprises cannabidiol and wherein said therapeutic composition comprises at least 0.1 parts per million cannabidiol and less than 1% by weight cannabidiol.

Additional embodiments also include: a pharmaceutical product comprising a therapeutic composition produced according to the method described above is also described; a method of treating a medical condition comprising administering to a subject an effective amount of a pharmaceutical product described above is also described; the method described above where said pharmaceutical product has an enhanced therapeutic effect, compared with that of a composition comprising the same cannabinoids amounts prepared without applying the enzyme; and the method described above where said enhanced therapeutic effect, is selected from treating a condition selected from the group consisting of from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease

DETAILED DESCRIPTION OF THE INVENTION

Unless otherwise defined, percent is weight percent and ratio is weight/weight ratio. Unless otherwise defined, weight ratio means the ratio between weight content, e.g. in an aqueous solution containing 20% solute and 80% water, the solute to water weight ratio is 20:80 or 1:4.

Unless otherwise specifically defined naming a cannabinoid refers to its acid form (cannabidiolic acid, CBDa), to its non-acid (decarboxylated) form (cannabidiol, CBD) or to a combination of the two.

As used herein, water activity (Aw) of a composition refers to the ratio between water partial vapor pressure of said composition and the partial vapor pressure of pure water at the same temperature. As used herein, low water activity (low Aw) refers to water activity of less than 0.8 (Aw<0.8).

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Provided herein is a therapeutic composition comprising (i) water at a concentration in the range of up to 30%, (ii) glucose, (iii) at least 5 parts per million (ppm) glucose reaction product other than sucrose and fructose; (iii) a selected amount of a cannabinoid, (iv) at least 1 ppm cannabinoid reaction product; optionally (v) a terpene and optionally (vi) at least 1 ppm terpene reaction product.

According to an embodiment, said therapeutic composition is capable of relieving a medical situation, e.g. illness or pain, is capable of relieving conditions resulting from a medical treatment and/reduction of secondary adverse symptoms, e.g. adverse symptoms of the main illness, or of another illness.

According to an embodiment, said therapeutic composition is dry or almost dry, e.g. containing 0.01% or 0.015% water. According to another embodiment, water content there is less than 30%, less than 26%, less than 24%, less than 22%, less than 20%, less than 19%, less than 18%, less than 17%, less than 16%, less than 15%, less than 14%, less than 13%, or less than 12%.

According to an embodiment, said therapeutic composition comprises glucose. According to an embodiment, said therapeutic composition includes sucrose. According to an embodiment, said therapeutic composition includes at least 1% sucrose.

According to an embodiment, said therapeutic composition comprises at least 5 ppm glucose reaction product other than sucrose and fructose, at least 10 ppm, at least 15 ppm, at least 20 ppm, at least 25 ppm, at least 30 ppm, at least 35 ppm, at least 40 ppm, at least 45 ppm or at least 50 ppm. As used herein glucose reaction product refers to a compound that can be produced from glucose in a chemical or an enzymatic reaction. According to an embodiment said chemical or enzymatic reaction comprises glucose oxidation and said glucose reaction product is also referred to as glucose oxidation product. According to an embodiment, said glucose reaction product comprises glucono-lactone, gluconic acid and combinations thereof.

According to an embodiment, the glucose to glucose reaction product weight/weight ratio is in the range of between 1 and 1000 According to an embodiment, the glucose to glucose reaction product weight/weight ratio is greater than 1, greater than 2, greater than 3 greater than 5, greater than 6, greater than 7, greater than 8 greater than 9, or greater than 10. According to an embodiment, the glucose to glucose reaction product weight/weight ratio is less than 1000, less than 900, less than 800, less than 700, less than 600, less than 500, less than 400, less than 300, less than 200 or less than 100. According to an embodiment, said therapeutic composition comprises a selected amount of a cannabinoid. As known in the art, cannabinoids have an acid form and a non-acid form (which is also referred to as decarboxylated form, since it can be generated by decarboxylating the acid form). The acid form is indicated herein by the letter (a) at the end of the cannabinoid acronym, e.g. tetrahydrocannabiniolic acid is indicated as THCa, while the decarboxylated form is THC. According to an embodiment, said cannabinoids are selected from the group consisting of tetrahydrocannabiniol in acid or decarboxylated form (THCa or THC, respectively), cannabidiol in acid or decarboxylated form (CBDa or CBD, respectively), cannabigerol in acid or decarboxylated form (CBGa or CBG, respectively), cannabichromene in acid or decarboxylated form (CBCa or CBC, respectively) tetrahydrocannabivarin in acid or decarboxylated form (THCVa or THCV, respectively), Cannabidivarin in acid or decarboxylated form (CBDVa or CBDV respectively) and cannabinol in acid or decarboxylated form (CBNa or CBN, respectively).

According to an embodiment, at least one of said cannabinoids is in acid form. According to an embodiment, at least one of said cannabinoids is at least partially in decarboxylated form. According to an embodiment, at least 50% of said cannabinoid is in decarboxylated form, at least 60%, at least 70%, at least 80% or at least 90%.

According to an embodiment, said cannabinoid includes tetrahydrocannabinol and said therapeutic composition comprises at least 0.1 parts per million (ppm) and less than 2% THCa and/or THC. According to an embodiment, said therapeutic composition comprises at least 0.1 ppm THCa and/or THC, at least 0.5 ppm, at least 1 ppm, at least 2 ppm, at least 3 ppm, at least 4 ppm or at least 5 ppm. According to an embodiment, said therapeutic composition comprises less than 2% THCa and/or THC, less than 1.6%, less than 1.2%, less than 1%, less than 0.8%, less than 0.6%, less than 0.4%, less than 0.2%, or less than 0.1%.

According to an embodiment, said cannabinoid includes cannabidiol said therapeutic composition comprises at least 0.1 ppm and less than 2% CBDa and/or CBD. According to an embodiment, said therapeutic composition comprises at least 0.1 ppm CBDa and/or CBD, at least 0.5 ppm, at least 1 ppm, at least 2 ppm, at least 3 ppm, at least 4 ppm or at least 5 ppm. According to an embodiment, said therapeutic composition comprises less than 2% CBDa and/or CBD, less than 1.6%, less than 1.2%, less than 1%, less than 0.8%, less than 0.6%, less than 0.4%, less than 0.2%, or less than 0.1%.

According to an embodiment, said composition comprises both CBD and/or CBDa and THC and/or THCa and the weight/weight ratio between CBD and/or CBDa and THC and/or THCa ((CBD+CBDa)/(THC+THCa)) is at least 10, at least 15, at least 20, at least 25 or at least 30.

According to an embodiment, said therapeutic composition further comprises at least 1 ppm cannabinoid reaction product, at least 2 ppm, at least 3 ppm, at least 3 ppm, at least 5 ppm, at least 6 ppm, at least 7 ppm, at least 8 ppm, at least 9 ppm or at least 10 ppm. As used herein cannabinoid reaction product refers to a compound that can be produced from a cannabinoid in a chemical or an enzymatic reaction. According to an embodiment said chemical or an enzymatic reaction comprises cannabinoid oxidation and said glucose reaction product is also referred to as cannabinoid oxidation product. According to an embodiment, said cannabinoid reaction product comprises a compound that can be produced from a cannabinoid selected from the group consisting of THC, THCa, CBD, CBDa and combinations thereof. According to an embodiment, said cannabinoid reaction product is a cannabinoid. According to an embodiment, said cannabinoid reaction product is a compound that can be produced by cannabinoid oxidation.

According to an embodiment, the cannabinoid to cannabinoid reaction product weight/weight ratio is in the range of between 1 and 1000 According to an embodiment, the cannabinoid to cannabinoid reaction product weight/weight ratio is greater than 1, greater than 2, greater than 3 greater than 5, greater than 6, greater than 7, greater than 8 greater than 9, or greater than 10. According to an embodiment, the cannabinoid to cannabinoid reaction product weight/weight ratio is less than 1000, less than 900, less than 800, less than 700, less than 600, less than 500, less than 400, less than 300, less than 200 or less than 100.

According to an embodiment, said therapeutic composition comprises a terpene. The term "terpene", as used herein, refers to both terpenes and terpenoids. According to an embodiment, said terpene is selected from the group consisting of pinene, limonene, linalool, caryophyllene, myrcene, humulene, borneol, eucalyptol, terpineol, nerolidol, phytol, geraniol, bisabolol, camphene, beta-amyrin, thujone, citronellol, pulegone, 1,8-cineole, cycloartenol, isomers thereof and combinations thereof.

According to an embodiment, said therapeutic composition further comprises at least 1 ppm terpene reaction product, at least 2 ppm, at least 3 ppm, at least 3 ppm, at least 5 ppm, at least 6 ppm, at least 7 ppm, at least 8 ppm, at least 9 ppm or at least 10 ppm. As used herein terpene reaction product refers to a compound that can be produced from a terpene in a chemical or an enzymatic reaction. According to an embodiment said chemical or an enzymatic reaction comprises terpene oxidation and said glucose reaction product is also referred to as terpene oxidation product. According to an embodiment, said terpene reaction product comprises a compound that can be produced from a terpene selected from the group consisting of pinene, limonene, linalool, caryophyllene, myrcene, humulene, borneol, eucalyptol, terpineol, nerolidol, phytol, geraniol, bisabolol, camphene, beta-amyrin, thujone, citronellol, pulegone, 1,8-cineole, cycloartenol and combinations thereof. According to an embodiment, said terpene reaction product is a terpene. According to an embodiment, said terpene reaction product is a compound that can be produced by terpene oxidation.

According to an embodiment, the terpene to terpene reaction product weight/weight ratio is in the range of between 1 and 1000 According to an embodiment, the terpene to terpene reaction product weight/weight ratio is greater than 1, greater than 2, greater than 3 greater than 5, greater than 6, greater than 7, greater than 8 greater than 9, or greater than 10. According to an embodiment, the terpene to terpene reaction product weight/weight ratio is less than 1000, less than 900, less than 800, less than 700, less than 600, less than 500, less than 400, less than 300, less than 200 or less than 100.

According to an embodiment, said therapeutic composition is homogeneous As used herein, homogeneous means having a consistent distribution of said cannabinoid, as a solute or as an emulsion.

According to an embodiment, said therapeutic composition is a humans medication. According to an embodiment, said therapeutic composition is a veterinary medication.

According to an embodiment, the shelf life of said therapeutic composition is at least 6 months or at least a year. According to an embodiment, the shelf life of said therapeutic composition is at 10% greater than that of a composition comprising the same cannabinoid amounts, but not said glucose reaction product, at least 20% greater, at least 30%, at least 40%, at least 50% or at least 60% greater.

According to an embodiment, said therapeutic composition, has an enhanced therapeutic effect compared with that of a composition comprising the same cannabinoid amounts, but not said glucose reaction product. According to an embodiment, said enhanced therapeutic effect is selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

According to an embodiment, said therapeutic composition contains a selected amount of a cannabinoid reaction product, which product is a cannabinoid oxidation product, and has an enhanced therapeutic effect, compared with that of a composition comprising the same cannabinoid amounts and no cannabinoid product. According to an embodiment, said enhanced therapeutic effect is selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

According to an embodiment, said therapeutic composition, contains a selected amount of a terpene reaction product and has an enhanced therapeutic effect, compared with that of a composition comprising the same cannabinoid amounts and no terpene reaction product. According to an embodiment, said enhanced therapeutic effect is selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

According to an embodiment, said therapeutic composition, contains a selected amount of a reaction product selected from the group consisting of glucose reaction product, cannabinoid oxidation product and terpene reaction product and said therapeutic composition has an enhanced therapeutic effect, compared with that of a composition comprising the same cannabinoid amounts and none said reaction product.

According to various embodiment, said increased therapeutic effect has various forms, e.g. a shorter onset time, increased magnitude, extended duration, reduced dosages, reduced secondary adverse symptoms, and combinations thereof. According to an embodiment, said increased therapeutic effect comprises a shorter onset time, or differently put an earlier effect, which is important particularly in cases of sublingual and topical delivery and in cases where a rapid effect is desired, as in treating pain. According to an embodiment, the onset time, as measured by methods known in the art, is at least 20% shorter, at least 30%, at least 40%, at least 50% or at least 60% shorter. According to an embodiment, said increased therapeutic effect comprises extended duration of the therapeutic effect, for example an extended time of pain relief. According to an embodiment, the duration of the therapeutic effect, as measured by methods known in the art, is at least 20% greater, at least 30%, at least 40%, at least 50% or at least 60% greater.

According to an embodiment, said increased therapeutic effect comprises increased magnitude of the therapeutic effect, enabling achieving a desired therapeutic effect on administering smaller doses of cannabinoids, saving thereby on cost. According to an embodiment, the magnitude of the therapeutic effect, as measured by methods known in the art, is at least 20% greater, at least 30%, at least 40%, at least 50% or at least 60% greater. Without wishing to be limited by any particular theory, such increased magnitude of the therapeutic effect may indicate increased bioavailability. Such increased magnitude enables achieving a desired therapeutic effect on administering smaller doses of cannabinoids, saving thereby on cost. According to an embodiment, said increased therapeutic effect comprises reduction of secondary adverse symptoms, e.g. adverse symptoms of the main illness, of ones of another illness and/or ones related to administered said composition or other drugs.

According to an embodiment, said enhanced therapeutic effect is observed in treating at least one condition selected from the group consisting of post trauma syndrome disorder (PTSD), anxiety, depression, psychosis syndromes, autism, autism spectrum disorder, Alzheimer's disease, Parkinson disease, inflammation, including inflammation from multiple sclerosis, spasticity and muscle tension including spasticity and muscle tension from multiple sclerosis, Parkinson disease, Huntington's disease and Dystonia, pain, including pain from multiple sclerosis, Parkinson disease and Alzheimer's disease, epilepsy, stroke, traumatic brain injury, bronchial disorders including asthma, cancer and cancer related symptoms, drug abuse, Huntington's disease, Dystonia, Amyotrophic lateral sclerosis (ALS), Tourette syndrome, Myasthenia gravis, sleep disorders, skin related syndromes, including acne, inflammatory bowel disease, macular degeneration, glaucoma and osteoporosis.

According to an embodiment, further provided is a product comprising tablets, gel capsules, suppositories, energy drinks, bakery products, medical patches, cigarettes and vaporizer liquids containing said therapeutic composition.

According to an embodiment, further provided is a method of treating a medical condition comprising administering to a subject an effective amount of said therapeutic composition described herein. According to an embodiment, said medical condition is selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

According to an embodiment, said administering comprises at least one of sublingual administering, oral administering and topical administering.

According to an embodiment, said therapeutic composition, additionally contains a non-cannabis pharmaceutical compound. As used herein non-cannabis pharmaceutical compound refers to a pharmaceutical compound other than those typically found in extracts of cannabis plant materials. According to an embodiment, further provided is a method of treating a medical condition comprising administering to a subject an effective amount of said additionally containing a non-cannabis pharmaceutical compound therapeutic composition. According to an embodiment, said medical condition is selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

Further provided is a method for producing a therapeutic composition, comprising (i) providing a glucose-containing composition; (ii) providing a cannabinoid-containing composition; (iii) blending said glucose-containing composition with said cannabinoid-containing composition to form cannabinoid-enriched glucose composition; and (iv) applying an enzyme at a selected temperature, a selected pH, and a selected water activity and for a selected duration, in said cannabinoid-enriched glucose composition whereby an enzymatically-catalyzed conversion of at least one of glucose and cannabinoid is affected, and optionally (v) water removal from said cannabinoid-enriched glucose composition, in said cannabinoid-enriched glucose composition, wherein said temperature, pH, water activity and duration are selected to enzymatically catalyze the conversion of at least 0.1% by weight of said glucose, said cannabinoid or both.

According to an embodiment, said applied enzyme is a honey enzyme. According to an embodiment, said honey enzyme is selected from the group consisting of glucose oxidase, invertase, diastase, catalase, acid phosphatase and combinations thereof. According to an embodiment, said applied enzyme comprises a non-honey enzyme. According to an embodiment, said applied enzyme comprises a honey enzyme and a non-honey enzyme.

According to an embodiment, glucose concentration in said glucose-containing composition, in said cannabinoid-enriched glucose composition, or in both is greater than 30%, greater than 40%, greater than 50%, greater than 60%, greater than 70%, greater than 75% or greater than 80%. According to an embodiment, said glucose-containing composition additionally includes sucrose, e.g. at least 2%, at least 5%, at least 10%, at least 15%, at least 20%, or at least 25%.

According to an embodiment, water concentration in said glucose-containing cannabinoid-enriched glucose composition, is less than 60%, less than 50%, less than 40%, less than 35%, less than 30%, less than 25%, less than 20%, less than 18% less than 16%, less than 14% or less than 12%.

According to an embodiment, glucose to water weight/weight ratio in said cannabinoid-enriched glucose composition is greater than 2, greater than 2.5, greater than 3, greater than 3.5, greater than 4, greater than 4.5 or greater than 5.

According to an embodiment, said glucose-containing composition comprises honey. According to an embodiment, said glucose-containing composition is honey. According to an embodiment, said glucose-containing composition is diluted honey. According to an embodiment, said glucose-containing composition is honey diluted with water.

According to an embodiment, said cannabinoid comprises said cannabinoid decarboxylated or the acid form.

According to an embodiment, said cannabinoid is selected from the group consisting of acid and decarboxylated forms of tetrahydrocannabinol (THCa and THC), cannabidiol (CBDa and CBD, respectively), cannabigerol (CBGa and CBG, respectively), cannabichromene (CBCa and CBC, respectively) tetrahydrocannabivarin (THCVa and THCV, respectively) Cannabidivarin (CBDVa and CBDV, respectively), cannabinol (CBNa and CBN, respectively) and combinations thereof. According to an embodiment, said cannabinoid-enriched glucose composition comprises THC. According to an embodiment, said cannabinoid-enriched glucose composition comprises CBD.

According to an embodiment, said cannabinoid-containing composition is an extract of cannabis plant. According to an embodiment, providing said cannabinoid-containing composition comprises extracting a cannabis plant material. As used herein, the term cannabis plant material refers to any part of the cannabis plant, e.g. its flower. According to an embodiment, said extracting comprises steam distillation. According to an embodiment, said extracting comprises contacting a cannabis plant material with a liquid extractant, e.g. ethanol, a liquefied gas, such as butane, butene or dimethyl-ether, liquefied $CO_2$, super-critical $CO_2$, sub-critical $CO_2$ or near-critical $CO_2$. According to an embodiment, the formed extract is provided as such. According to an alternative embodiment, said extract is mixed with a solvent to form a solvent-comprising extract. According to an alternative embodiment, said cannabinoid-containing composition comprises at least 10% of a solvent, at least 20%, at least 30% or at least 40%. According to an embodiment, said solvent is selected from a group consisting of terpenes, flavonoids, vegetable oils and combinations thereof. According to an embodiment, said providing said cannabinoid-containing composition includes at least partially decarboxylating said cannabinoid in said extract or in said solvent-comprising extract. According to an embodiment, said decarboxylating comprises a thermal treatment.

According to an embodiment, said providing said cannabinoid-containing composition comprises analyzing said extract or said solvent-comprising extract.

According to an embodiment, said blending comprises mixing said glucose composition with said cannabinoid-containing composition to form said cannabinoid-enriched glucose composition.

According to an embodiment, said cannabinoid-enriched glucose composition is homogenous. As used herein, homogeneous means having a consistent distribution of said cannabinoid, as a solute or as an emulsion. According to an embodiment, said blending is conducted at a temperature and at water activity (Aw) enabling the formation of homogeneous cannabinoid-enriched glucose composition.

As used herein, Aw of a composition refers to the ratio between water partial vapor pressure of said composition and the partial vapor pressure of pure water at the same temperature. Aw typically increases with increasing water concentration and typically decreases with increasing concentration of a hydrophilic solute, such as glucose, and with increasing concentration of an electrolyte, such as NaCl. For example, Aw of pure water, saturated NaCl solution and honey are 1.0, 0.75 and 0.5-0.7, respectively. Cannabinoids are lipophilic in nature and do not dissolve in compositions of relatively high Aw. As a result, cannabinoid solubility improves with increasing glucose concentration. Suitable Aw and suitable glucose concentrations for homogeneous blending with said cannabinoid-containing composition depend on the nature of the latter and can be found in mixing tests.

Solutions with high glucose concentration, such as honey, are viscous. Temperature elevation reduces said viscosity and facilitate said blending. According to an embodiment, during said blending, the temperature of said glucose-containing composition is in the range between 30° C. and 70° C., between 35° C. and 65° C., or between 37° C. and 60° C.

A lipophilic compound such as a cannabinoid can be homogeneously blended also with a solution of a relatively high Aw, when a suitable emulsifier is used. According to an embodiment, said blending comprises adding an emulsifier. According to an embodiment, said emulsifier is mixed with said cannabinoid-containing composition before contacting with said glucose composition. According to an embodiment, said blending comprises mixing said glucose composition, said cannabinoid-containing composition and said emulsifier to form said cannabinoid-enriched glucose composition. According to an embodiment, said emulsifier is a food-approved emulsifier. According to an embodiment, said emulsifier is selected from the group consisting of polysorbates, glycolipids, phospholipids and their mixtures.

According to an embodiment, cannabinoid concentration in said cannabinoid-enriched glucose composition is less than 10,000 ppm, less than 5,000 ppm, less than 2,000 ppm, less than 1,000 ppm, less than 500 ppm or less than 250 ppm. According to an embodiment, cannabinoid concentration in said cannabinoid-enriched glucose composition is greater than 1 ppm, greater than 5 ppm, greater than 10 ppm, greater than 20 ppm, greater than 30 ppm, greater than 40 ppm, greater than 50 ppm, greater than 60 ppm, greater than 70 ppm, greater than 80 ppm, greater than 90 ppm or greater than 100 ppm. According to an embodiment, cannabinoid concentration in said cannabinoid-enriched glucose composition is in the range between 0.1 ppm and 250 ppm, between 0.5 ppm and 200 ppm, between 1 ppm and 200 ppm, between 1.5 ppm and 150 ppm or between 2 ppm and 100 ppm.

According to an embodiment, glucose to cannabinoid weight/weight ratio in said cannabinoid-enriched glucose composition is greater than 10, greater than 20, greater than 40, greater than 60, greater than 80, greater than 100 greater than 150, greater than 200 or greater than 250.

According to an embodiment, said method comprises applying an enzyme at a selected temperature, a selected pH, and a selected water activity and for a selected duration in said cannabinoid-enriched glucose composition, whereby an enzymatically-catalyzed conversion of at least one of glucose and cannabinoid is affected and wherein said temperature, pH, water activity and duration are selected to enzymatically-catalyze the conversion of at least 0.1% by weight of said glucose, said cannabinoid or both. As used herein, applying an enzyme refers to bringing in contact, e.g. mixing, with said enzyme or with an enzyme-comprising composition. As used herein, conversion means a reaction wherein said glucose, said cannabinoid or both are reacted to form a different compound.

According to an embodiment, glucose is converted to form glucono-lactone, gluconic acid or a combinations thereof.

According to an embodiment, said cannabinoid is converted to form another cannabinoid or one or more non-cannabinoid compound.

According to an embodiment, the degree of conversion of glucose and of said cannabinoid is determined by the change in their concentration compared with that prior to said applying said enzyme. According to an embodiment, at least 0.1% of the glucose is converted, at least 0.5%, at least 1%, at least 2%, at least 4%, at least 6%, at least 8%, at least 10% or at least 12%.

According to an embodiment, at least 0.1% of said cannabinoid is converted, at least 0.5%, at least 1%, at least 2%, at least 4%, at least 6%, at least 8%, at least 10% or at least 12%.

According to an embodiment, said cannabinoid-enriched glucose composition comprises at least two cannabinoids and both cannabinoids are converted.

According to an embodiment, the degree of conversion of one cannabinoid is greater than that of the other cannabinoid. According to an embodiment, said two cannabinoids are THC and CBD and the conversion of THC is greater than that of CBD.

According to an embodiment, said enzyme or a composition containing it is brought in contact with said cannabinoid-enriched glucose composition. Alternatively or additionally, according to an embodiment said enzyme or a composition containing it is brought in contact with said cannabinoid comprising composition prior to said blending and is kept active or made active while in the cannabinoid-enriched glucose composition. Alternatively or additionally, according to an embodiment said enzyme or a composition containing it is brought in contact with said glucose comprising composition prior to said blending and is kept active or made active while in the cannabinoid-enriched glucose composition.

According to an embodiment, said glucose-containing composition is honey and said honey contains honey enzymes and at least one of said enzymes is kept active or made active while in the cannabinoid-enriched glucose composition.

According to an embodiment, said glucose-containing composition, said enzyme composition and/or said cannabinoid-enriched glucose composition comprise a glucose oxidase.

According to an embodiment, said glucose-containing composition, said enzyme composition and/or said cannabinoid-enriched glucose composition comprise a glucose oxidase cofactor.

According to an embodiment, during said applying an enzyme, said treated composition is exposed to oxygen, e.g. to air.

According to an embodiment, said glucose-containing composition is a flower nectar and said nectar is contacted with said enzyme in honeybee honey stomach.

According to an embodiment, said nectar is converted by the honeybee into honey comprising said enzyme and said honey is blended with said cannabinoid-containing composition to form enzyme-containing cannabinoid-enriched glucose composition. As used herein, the term honeybee refers to any honey forming bee.

According to an embodiment, a supplemental enzyme is applied to said cannabinoid-enriched glucose composition.

Enzymes act as catalysts, catalyzing reactions such as glucose conversion and/or cannabinoid conversion. The activity of enzymes is dependent on parameters, such as pH, temperature and water activity (Aw). Typical enzyme activity decreases with increasing Aw. Each enzymes has its optimal pH and optimal temperature, wherein its activity is optimal. In a given composition and for a given reaction, increased enzyme activity increases reaction rate, which enables reaching a desired conversion in a shorter time. The opposite is true too. When enzyme activity is low, a given conversion might not be reached within an industrially attractive time.

According to an embodiment, said temperature, pH, water activity and duration are selected to catalyze the conversion of at least 0.1% by weight of said glucose, said cannabinoid or both.

According to an embodiment, said temperature, pH and water activity are selected to reach the desired conversion within a reasonable time, but not necessarily during minimal time.

According to an embodiment, said temperature, pH and water activity are selected to reach the desired degree of conversion within less than a week, less than 6 days, less than 5 days, less than 4 days, less than 3 days, less than 2 days, or less than one day.

According to an embodiment, in many cases, control of catalytic reaction temperature and its pH are limited, while control of Aw is easier. Thus, while optimal pH for each enzyme is known, pH adjustment of said cannabinoid-enriched glucose composition, e.g. by adding an acid, a base or a buffer might not be desired in many cases, e.g. where the natural form of the product is aimed. Additionally, pH control becomes more difficult with decreasing Aw (pH is in fact determined by the concentration of $H3O^+$). This is true, for example when honey is used as the glucose-containing composition. Some honey has slightly acidic pH. Thus, according to an embodiment, said applying an enzyme is conducted at a pH between 3 and 9 between 3.5 and 8, or between 4 and 7.

Typically, there is also a limited range for optimizing the temperature of said enzymatically-catalyzed reaction, particularly in cases of low Aw as in honey. At too low temperatures, e.g. less than 20° C., the cannabinoid-enriched glucose composition is highly viscous, which may lead to too low reaction rate (e.g. the desired conversion may take more than a week). At the same time, too high temperatures, e.g higher than 90° C., may deteriorate the nutritional value of the honey and/or to the loss of desired volatile components. Thus, according to an embodiment, said enzymatically-catalyzed conversion is conducted at a temperature between 20° C. and 70° C., between 25° C. and 60° C., or between 30° C. and 50° C. In contrary to temperature and pH, in many cases, water activity (Aw) is relatively easy to control and provides a useful tool to affect the rate, and through that and the reaction duration, to affect the degree of conversion. That is done by adjusting or maintaining the water content of the cannabinoid-enriched glucose composition, e.g. addition of water, maintaining water content (avoiding evaporation or making up for it) or adding water. Additionally, controlling water content enables modifying Aw during to the conversion, if desired.

According to an embodiment, honey is used as the glucose-containing composition and blended with the cannabinoid comprising composition to form said cannabinoid-enriched glucose composition. As indicated, Aw or honey is low and low Aw is required in order to form homogeneous cannabinoid-enriched glucose composition. As a result, the Aw of said formed cannabinoid-enriched glucose composition is low, e.g. <0.8. For enzymes already present in the honey and/or ones added to the cannabinoid-enriched glucose composition this Aw is too high so that the enzymatically-catalyzed conversion is too low for an industrial preparation, e.g. the desired degree of conversion requires duration time of more than 10 days or more than 20 days. According to an embodiment, the method includes inducing or facilitating said enzymatically-catalyzed conversion.

According to an embodiment, said inducing or facilitating comprises water addition to lower Aw. Due to the complex nature of the cannabinoid-enriched glucose composition, and since said composition may contain multiple enzymes, the amount of water to be added is difficult to determine on theoretical basis and is best determined experimentally. An exemplary experimental method is described below. Other methods may work too.

Thus, the exemplary experimental method involves: (I) Analysis of the glucose and the cannabinoid content in the cannabinoid-enriched glucose composition, with the enzyme it contains (naturally occurring and/or supplemented), using known methods. (II) Analysis of Aw there at the temperature selected for the industrial operation by using a conventional method. (III) Next, dividing the cannabinoid-enriched glucose composition into 5-10, numbered, test tubes, which are then sealed and gently shacked for 30 minutes in a water bath, wherein the temperature is adjusted to that selected for the industrial operation, say, 35° C. (IV) Then water is added to each one of the tubes, which are then sealed again. The amount added should form from about 5% to about 50% of the glucose content and should differ from one test tube to the other. (V) The tubes are sealed and shacked in the water bath for additional 30 minutes. (VI) The Aw is determined in each tube by said known method. (VII) The Aw data is used to calculate the amount of water to be added (or removed) in order to form cannabinoid-enriched glucose compositions with Aw of 0.8, 0.83, 0.86, 0.9, 0.92 and 0.94. (VIII) Based on the calculation in (VII) 6 test tubes are prepared containing diluted cannabinoid-enriched glucose compositions with Aw of 0.8, 0.83, 0.86, 0.9, 0.92 and 0.94, sealed and shacked in the water bath at the selected temperature. (IX) A sample is taken out of each one of the tubes every 6 hours for 5 days, and analyzed for its glucose and cannabinoid content. During the time between sampling and analysis, the sample is kept frozen. The analytical results are correct for the dilution by the added water. (X) The results in (IX) are used to calculate the effect of Aw on reaction kinetics and to select a suitable Aw fof the enzymatically-catalyzed conversion.

Using this exemplary experimental method, the skilled artesian may select the amount of water to be added in order to initiate of facilitate the enzymatically-catalyzed conversion in a low Aw cannabinoid-enriched glucose compositions, e.g. as the one produced by blending honey with said cannabinoid-containing composition.

According to another embodiment, there is a need to slow down said enzymatically-catalyzed conversion, e.g. when its rate is too high or when a selected degree of conversion is reached and further conversion is undesired. For example, according to an embodiment, said temperature, pH, water activity and duration are selected to enzymatically-catalyze the conversion of glucose, said cannabinoid or both to a degree of less than 50%, less than 40%, less than 30%, less than 20% or less than 10%.

According to another embodiment, avoiding too high conversion is done by selecting Aw wherein the enzyme catalysis is slow.

According to another embodiment, once the desire degree of conversion is reached, the conversion is stopped by removing water to reach Aw, wherein the enzyme activity is low or zero.

According to another embodiment, a glucose-containing composition of low Aw is blended with said cannabinoid comprising composition to form a low Aw cannabinoid-enriched glucose compositions, water is added to adjust the Aw, the temperature is adjusted to the desired temperature, enzyme is applied for a duration suitable to reach the desired conversion and then water is removed and/or the temperature is lower to reach conditions where enzyme activity is small or zero.

According to another embodiment said glucose-containing composition of low Aw is honey which already contains enzymes. Optionally, supplemented enzyme is added.

According to another embodiment said applying an enzyme is done in the honeybee body, more specifically in the honey stomach where typically nectar is collected and brought into the beehive.

According to another embodiment said cannabinoid-enriched glucose compositions is fed to bees near the beehive and/or in it. Bees collect it in the honey stomach, add to it enzymes and then store it in the honeycomb cells. This way of conducting the method of the present invention is interesting, but face a combination of Aw-related difficulties to which a person skilled in the art might not be aware: (I) In case of too high Aw in forming the cannabinoid-enriched glucose compositions doesn't allow the formation of a homogeneous composition, cannabinoid might separate out and not be included in the composition taken into the bees honey stomach. The composition formed in this case might have too little cannabinoid. (II) In case of too low Aw in cannabinoid-enriched glucose compositions collected by the honeybee, enzyme activity would be too low and the desired degree of enzymatically-catalyzed conversion would not be reached. (III). Flower nectar is typically of about 20% carbohydrate concentration and is rapidly dried to >80% carbohydrate concentration before stored in the beehive honeycomb or simultaneously with said storing. The amount of water to be removed is relatively large (about 4 weight of water per weight of honey formed) and bees to that very efficiently. Hence honeybees collecting said cannabinoid-enriched glucose compositions might dry it too quickly to reach Aw where enzyme activity is too low.

Hence, according to another embodiment, said glucose-containing composition and said cannabis containing composition are blended to form a cannabinoid-enriched glucose compositions wherein Aw is at the higher end of the range where homogeneous mixing is capable.

According to an embodiment, the specific Aw is determined experimentally for each type of glucose-containing composition and said cannabis containing composition.

According to an embodiment, the formed cannabinoid-enriched glucose compositions is fed to bees at conditions where drying is sufficiently slow to provide sufficient time at sufficiently high Aw to achieve the desired degree of conversion.

According to an embodiment, the formed cannabinoid-enriched glucose compositions is fed to bees in an environment with high relative moisture (e.g. as in a moisture a controlled environment).

According to an embodiment, moisture is brought down when desired conversion is gained, e.g. by artificial drying.

According to an additional embodiment, enzymes comprising honey is used as said glucose-containing composition, Aw is adjusted to a desired level and the formed cannabinoid-enriched glucose composition is kept for a duration sufficient to enable enzymatically catalyzed conversion before being fed to the honeybees. Further provided is pharmaceutical product comprising said therapeutic composition. According to an embodiment said product is selected from the group consisting of capsules, tablets, droplets, bakery products and candies.

According to an embodiment said product further comprises a pharmaceutical compound.

According to an embodiment, said pharmaceutical product comprises at least 0.1 ppm THC, at least 0.5 ppm, at least 1 ppm, at least 5 ppm, at least 15 ppm or at least 20 ppm. According to an embodiment, said pharmaceutical product comprises less than 1000 ppm THC, less than 800 ppm, less than 600 ppm, 400 ppm, less than 200 ppm, less than 100 ppm or less than 50 ppm.

According to an embodiment, said pharmaceutical product comprises at least 0.1 ppm CBD, at least 0.5 ppm, at least 1 ppm, at least 5 ppm, at least 15 ppm or at least 20 ppm.

According to an embodiment, said pharmaceutical product comprises less than 1000 ppm CBD, less than 800 ppm, less than 600 ppm, 400 ppm, less than 200 ppm, less than 100 ppm or less than 50 ppm.

According to an embodiment, said pharmaceutical product comprises said therapeutic composition diluted with honey.

Further provided is a method of treating a medical condition comprising administering to a subject in need thereof an effective amount of said pharmaceutical product.

According to an embodiment, said composition is administered in a form selected from the group consisting of cigarettes, vaporizer plant material, vaporizer liquid, extract, tablets, gel capsules, suppositories and combinations thereof.

According to an embodiment, said pharmaceutical product has an enhanced therapeutic effect, compared with that of a composition comprising the same cannabinoids amounts, which composition is produced by blending the glucose-containing composition with the cannabinoid-containing composition without applying the enzyme.

According to an embodiment, said enhanced therapeutic effect, is selected from treating a condition selected from the group consisting of from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease The reason for the enhanced therapeutic effect is not entirely clear. Without wishing to be limited by any particular theory, one theory could be related to some new components of the composition, e.g. the product of glycose conversion and/or secondary products thereof, the product of the cannabinoid conversion and/or secondary products thereof, complexes formed by one of those conversion products or by both, complexes of the secondary products and combinations thereof. There could however be other explanations as well, e.g. some rearrangements taking place as a result of applying said enzymes, e.g. the formation of micro-emulsions.

According to an embodiment, said method of treating a medical condition comprises preparing multiple pharmaceutical products from multiple therapeutic compositions, which differ from each other in at least one of Aw and cannabinoid concentration in said cannabinoid-enriched glucose composition and administering to a subject in need thereof an effective amount of thereby formed therapeutic compositions to find the ones that are most suitable Examples 1-11

Table 1 presents examples of therapeutic composition preparations[1].

TABLE 1

| Preparation # | Glucose Content (%) | Glucose product Content (ppm) | Cannabinoid | Cannabinoid Content (%) | Cannabinoid product Content (ppm) | Terpene Content (%) | Terpene product Content (ppm) | Water[2] Content (%) | Excipients (%)[3] |
|---|---|---|---|---|---|---|---|---|---|
| 1 | 83 | 104 | THC | 1.1 | 12 | 0.6 | 3 | 13.4 | 0 |
| 2 | 65 | 23 | THC | 2 | 7 | 0.3 | 2 | 0.2 | 29.3 |
|   |    |    | CBD | 0.1 |   |   |   |   |   |
| 3 | 74 | 98 | THC | 0.1 | 2 | 0 | 0 | 11.1 | 12.6 |
| 4 | 78 | 63 | THC | 4.7 | 61 | 1.8 | 8 | 14.9 | 0 |
| 5 | 22 | 14 | THCa + CBD | 0.8 | 7 | 0.2 | 0 | 0.9 | 73.8 |
| 6 | 86 | 74 | CBD | 0.3 | 13 | 0.08 | 0 | 12.8 |   |
| 7 | 68 | 44 | THC | 0.015 | 2 | 0 | 0 | 0.1 | 30.4 |
| 8 | 53 | 69 | THC | 0.2 | 23 | 0.1 | 1 | 8.7 | 35.6 |
|   |    |    | CBD | 1.2 |   |   |   |   |   |
| 9 | 28 | 19 | CBDa | 0.7 | 31 | 0.05 | 0 | 0.3 | 67.7 |
| 10 | 84 | 107 | CBD | 0.012 | 3 | 0 | 0 | 15.1 | 0 |
| 11 | 81 | 57 | CBD | 2.6 | 17 | 0.3 | 2 | 15.3 | 0 |

[1]Total is less than 100% due to additional components, mainly co-extracted from *cannabis* plant material
[2]As determined by loss on drying
[3]Total amount of pharmaceutical excipients, solvents and emulsifiers Examples 12-22

Table 2 presents effective amounts of the therapeutic composition preparations of Table 1

TABLE 2

| Example | Preparation number in Table 1 | Effective amount in grams |
|---|---|---|
| 12 | 1 | 0.15 |
| 13 | 2 | 0.1 |
| 14 | 3 | 0.7 |
| 15 | 4 | 0.1 |
| 16 | 5 | 0.2 |
| 17 | 6 | 0.3 |
| 18 | 7 | 5 |
| 19 | 8 | 0.15 |
| 20 | 9 | 0.2 |
| 21 | 10 | 5 |
| 22 | 11 | 0.1 |

Examples 23-26

Cannabis plants of various strains were extracted using ethanol at ethanol to plant material weight/weight ratio of 8 to 1 for 30 minutes. Ethanol was removed from the extracts by evaporation under reduced pressure and the desolventized extracts were treated at 120° C. to reach complete decarboxylation. The cannabinoids content in each of the formed extracts was analyzed using HPLC.

Pure honey samples were blended with water and with the cannabis extracts to form what looked to the eye as homogeneous blends. Comparative blends were prepared by blending honey samples with extracts, but with no water addition. Cannabinoids concentrations in the blends were calculated, using the extracts compositions and the dilution by honey and water.

The blends were stored at room temperature for different durations. Then samples were taken and analyzed for cannabinoids content. The results are summarized in Table 3.

| Blends preparation | | | | Initial concentrations (calculated) | | Storage time | Concentrations after storage | | |
|---|---|---|---|---|---|---|---|---|---|
| Honey (gr) | Water (gr) | Extract (mg) | Glucose (calculated) % | THC (ppm) | CBD (ppm) | (days) | THC | CBD | Conversion |
| 30 | 10 | 49 | 64 | 752 | | 11 | 414 | | 45 |
| 30 | 10 | 51 | 64 | | 749 | 11 | | 547 | 27 |
| 30 | 0 | 49 | 85 | | 1150 | 18 | | 1148 | |
| 30 | 0 | 51 | 85 | 1050 | | 18 | 1047 | | |

These results demonstrate that at the low water activities of undiluted honey blends, conversion is insignificant. On water addition, water activity increases and along with it increases the conversion of the cannabinoids. THC conversion is greater than that of CBD.

Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A therapeutic composition comprising:
   (i) water at a concentration in the range of up to 30% by weight;
   (ii) at least 30 wt % glucose;
   (iii) at least 5 parts per million of a product of glucose oxidation selected from the group consisting of glucono-lactone, gluconic acid and combinations thereof;
   (iv) a cannabinoid selected from the group consisting of THC, THCa, CBD, CBDa and combinations thereof at a concentration in the range of from at least 0.1 parts per million (ppm) to less than 20,000 ppm by weight;
   (v) at least 1 part per million of a product of cannabinoid oxidation that can be produced from a same said cannabinoid selected from the group consisting of THC, THCa, CBD, CBDa and combinations thereof;
   (vi) a honey enzyme;
   optionally (vii) a terpene;
   optionally (viii) at least 1 parts per million terpene oxidation product, and;
   optionally a product of terpene oxidation,
   wherein a glucose to glucose oxidation product weight/weight ratio is in the range of between 10 and 1000,
   wherein a glucose to cannabinoid weight/weight ratio is greater than 10,
   wherein a weight/weight ratio of said cannabinoid to said product of oxidation of said same cannabinoid is in the range of between 10 and 1000, and
   wherein the composition is homogeneous.

2. The therapeutic composition of claim 1, having an enhanced therapeutic effect compared with that of a composition comprising the same cannabinoid amounts, but not containing said product of glucose oxidation and not containing said cannabinoid reaction product and optionally not containing said terpene oxidation product.

3. The therapeutic composition of claim 2, wherein said therapeutic effect, is for treating a condition selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease.

4. A method of treating a medical condition selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease, the method comprising administering to a subject an effective amount of the therapeutic composition of claim 1.

5. A method for producing the therapeutic composition of claim 1, comprising
   (i) providing a glucose-containing composition;
   (ii) providing a cannabinoid-containing composition;
   (iii) blending said glucose-containing composition with said cannabinoid-containing composition to form cannabinoid-enriched glucose composition;
   (iv) applying an enzyme at a selected temperature, a selected pH, and a selected water activity and for a selected duration, to said cannabinoid-enriched glucose composition, wherein said applying an enzyme comprises inducing enzyme activity and wherein said inducing comprises water addition, whereby an enzymatically-catalyzed conversion of at least one of glucose and cannabinoid is produced and optionally
   (v) removing water from said cannabinoid-enriched glucose composition;
   wherein said temperature, pH, water activity and duration are selected to enzymatically-catalyze the conversion of at least 0.1% by weight of said glucose, said cannabinoid or both.

6. The method of claim 5, wherein said temperature, pH, and water activity are selected to reach the desired degree of conversion within a duration of less than a week.

7. The method of claim 5, wherein said applied enzyme is a honey enzyme.

8. The method of claim 5, wherein glucose to water weight/weight ratio in said cannabinoid-enriched glucose composition is greater than 2.

9. The method of claim 5, wherein said glucose-containing composition additionally contains sucrose.

10. The method of claim 5, wherein said glucose-containing composition comprises honey.

11. The method of claim 5, wherein the glucose to cannabinoid weight/weight ratio in said cannabinoid-enriched glucose composition is greater than 10.

12. The method of claim 5, wherein said selected temperature is in the range of between 20° C. and 70° C.

13. The method of claim 5, including additionally blending said cannabinoid-enriched glucose composition with a non-cannabis pharmaceutical compound.

14. A pharmaceutical product comprising a therapeutic composition produced according to a method comprising:
   (i) providing honey;
   (ii) providing a cannabinoid-containing composition
   (iii) blending said honey with said cannabinoid-containing composition to form cannabinoid-enriched honey;
   (iv) activating an enzyme present in said honey by adding water to provide a selected water activity at a selected temperature, a selected pH and for a selected duration; and
   (v) removing water from said cannabinoid-enriched honey, whereby an enzymatically-catalyzed conversion of at least one of glucose present in said honey and cannabinoid is produced,
   wherein said temperature, pH, water activity and duration are selected to enzymatically-catalyze the conversion of at least 0.1% by weight of said glycose glucose present in said honey, said cannabinoid or both.

15. A method of treating a medical condition selected from the group consisting of post trauma syndrome disorder (PTSD), anxiety, depression, psychosis syndromes, autism, Alzheimer's disease, Parkinson disease, inflammation, spasticity and muscle tension, pain, epilepsy, stroke, traumatic brain injury, bronchial disorders, cancer, drug abuse, Huntington's disease, Dystonia, Amyotrophic lateral sclerosis (ALS), Tourette syndrome, Myasthenia gravis, sleep disorders and skin related syndromes and inflammatory bowel disease, the method comprising administering to a subject an effective amount of a pharmaceutical product according to claim 14.

16. The method of claim 15, wherein said pharmaceutical product has an enhanced therapeutic effect, compared with that of a composition comprising the same cannabinoids amounts prepared without applying the enzyme.

\* \* \* \* \*